United States Patent
Mandel et al.

(10) Patent No.: US 10,525,279 B2
(45) Date of Patent: Jan. 7, 2020

(54) APPARATUS AND METHOD FOR MULTIWAVELENGTH PHOTODYNAMIC THERAPY

(71) Applicant: Theralase Technologies, Inc., Toronto (CA)

(72) Inventors: Arkady Mandel, Toronto (CA); Roger Dumoulin-White, Toronto (CA); Wayne Embree, Toronto (CA)

(73) Assignee: Theralase Technologies, Inc., Toronto (CA)

( * ) Notice: Subject to any disclaimer, the term of this patent is extended or adjusted under 35 U.S.C. 154(b) by 507 days.

(21) Appl. No.: 15/307,686

(22) PCT Filed: Apr. 29, 2015

(86) PCT No.: PCT/IB2015/000597
§ 371 (c)(1),
(2) Date: Oct. 28, 2016

(87) PCT Pub. No.: WO2015/166333
PCT Pub. Date: Nov. 5, 2015

(65) Prior Publication Data
US 2017/0043179 A1    Feb. 16, 2017

Related U.S. Application Data

(60) Provisional application No. 61/986,071, filed on Apr. 29, 2014.

(51) Int. Cl.
*A61N 5/06*       (2006.01)
*A61K 41/00*    (2006.01)
*A61B 18/20*    (2006.01)
*A61N 5/067*    (2006.01)

(52) U.S. Cl.
CPC .......... *A61N 5/062* (2013.01); *A61K 41/0057* (2013.01); *A61N 5/0616* (2013.01); *A61B 2018/207* (2013.01); *A61B 2018/2065* (2013.01); *A61N 2005/067* (2013.01); *A61N 2005/0626* (2013.01); *A61N 2005/0651* (2013.01); *A61N 2005/0652* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| 5,130,997 | A | 7/1992 | Ortiz et al. |
| 5,998,597 | A | 12/1999 | Fisher et al. |
| 6,413,267 | B1 | 7/2002 | Dumoulin-White et al. |
| 2007/0219605 | A1 | 9/2007 | Yaroslavsky et al. |
| 2008/0119832 | A1* | 5/2008 | Cronin ................. A61B 5/0059 606/15 |
| 2011/0021970 | A1 | 1/2011 | Vo-Dinh et al. |
| 2011/0238137 | A1* | 9/2011 | Tsujita ................... A61N 5/062 607/88 |
| 2013/0035570 | A1* | 2/2013 | Miyasato ............. A61B 5/0095 600/323 |
| 2013/0041309 | A1 | 2/2013 | Siegel |
| 2013/0123648 | A1 | 5/2013 | Stampoulidis et al. |
| 2013/0331367 | A1* | 12/2013 | McFarland ......... C07F 15/0026 514/185 |

FOREIGN PATENT DOCUMENTS

| RU | 2328208 C1 | 7/2008 |
| RU | 112631 U1 | 1/2012 |
| UA | 82211 C2 | 3/2008 |

OTHER PUBLICATIONS

Lecture 21 Slides, Absorption and Transmission of Light and the Beer-Lambert Law; www.physic.uoguelph.ca/~pgarrett/Teaching. html PHY-1070 SG-6 Jun. 3, 2006 (Year: 2006).*
English Abstract for RU 112631 U1 (2012).
Pernot et al. (2012). Systems biology approach for in vivo photodynamic therapy optimization of ruthenium-porphyrin compounds. Journal of Photochemistry and Photobiology B: Biology, 117, 80-89.
International Search Report from PCT/IB2015/000597 dated Jul. 24, 2015.
Supplementary European Search Report from corresponding EP 15786751 dated Dec. 22, 2017.
Jing et al. (2003). An Unusual Photosensitizer: Dyad of Eosin-Tris(2,2'-bipyridine)Ru(II). Organic Letters, vol. 5 (20), 3709-3711.
Shi et al. (2014). Ru(II) dyads derived from alpha-oligothiophenes: a new class of potent and versatile photosensitizers for PDT. Coordination Chemistry Reviews, vol. 282-283, 127-138.
European Office Action dated Mar. 14, 2019.

* cited by examiner

*Primary Examiner* — Brian T Gedeon
(74) *Attorney, Agent, or Firm* — Caesar Rivise, PC

(57) ABSTRACT

A method for treating a condition in a tissue, includes the steps: (1) providing a PS within the tissue; (2) irradiating the tissue containing the PS with a first light of a first wavelength; and (3) irradiating the tissue containing the PS with a second light of a second wavelength so as to treat the condition in the tissue, wherein: (a) the PS absorbs light at the first wavelength and the second wavelength; and (b) the second light is more strongly absorbed by the tissue than the first light or vice versa, so as to achieve a predetermined absorbed photon density gradient. An apparatus for conducting the method includes first and second light sources, a power supply, a focusing device, and a controller which adjusts light emission such that $I(d)=I(\lambda 1$ at $d=0) \times \exp(\mu_{\textit{eff}}(\lambda 1) \times d) + I(\lambda 2$ at $d=0) \times \exp(\mu_{\textit{eff}}(\lambda 2) \chi d)$.

14 Claims, No Drawings

APPARATUS AND METHOD FOR MULTIWAVELENGTH PHOTODYNAMIC THERAPY

BACKGROUND OF THE INVENTION

1. Field of Invention

This invention relates to the use of photodynamic compounds as therapeutic agents and as in vivo diagnostic agents. In particular, the invention provides a method and system for applying radiation at selectable wavelengths and powers such that subsurface excitation of photodynamic compounds can be tuned.

2. Description of Related Art

Photodynamic therapy (PDT) is currently an active area of research for the treatment of diseases associated with unwanted and/or hyperproliferating cells such as cancer and non-malignant lesions. PDT has also found use in other contexts, including but not limited to the treatment of acne, psoriasis, proliferative non-malignant conditions, ulcers and wounds. The development of new photodynamic compounds ("PDCs") (or photosensitizers ("PSs")) for photodynamic therapy ("PDT") has been increasingly focused on metallosupramolecular complexes derived from metals such as ruthenium and rhodium. The ongoing investigation of new PSs for PDT stems from the limitations associated with traditional organic-based porphyrins such as PHOTOFRIN, which must be activated with relatively short wavelengths of light and do not function in hypoxic environments. Significant advances have been made toward overcoming these limitations with the introduction of mixed-metal complexes that possess low-lying $^3$MMCT (metal-to-metal charge transfer) excited states. To date, however, there has been limited reporting of PDCs, particularly those with a mononuclear or dinuclear design, that are capable of providing PDT for the treatment of diseases associated with unwanted and/or hyperproliferating cells, such as cancer and non-malignant lesions, and/or capable of treating other conditions; including, but not limited to infectious diseases and pathogen infections as well as sterilization.

There has been a long felt need for new PDCs that are useful as PSs for PDT that are both disease-modifying and effective in treating patients with diseases caused by unwanted and/or hyperproliferating cells, for example, cancer. There is also a long felt need for new PDCs that are useful as in vivo diagnostic agents. Moreover, it is desired to provide novel PDCs having: (1) increased photostability, (2) increased absorption at activation wavelength, (3) visible light, and preferably Near InfraRed ("NIR"), absorption, (4) maximal activity regardless of oxygen levels (possibly utilizing a mechanism for switching between Type 1 and Type 2 photosensitization), and (5) intracellular targeting.

U.S. Patent Application Publication No. 20130331367 proposes to address the need to develop novel PDCs that are useful as PSs for PDT that are both disease-modifying and effective in treating one or more of the conditions discussed above, such as treating patients with diseases caused by unwanted and/or hyperproliferating cells, for example, cancer.

BRIEF SUMMARY OF THE INVENTION

A first aspect of the invention comprises a method for treating a condition in a tissue, said method comprising the steps of:

providing a PS within the tissue;
irradiating the tissue containing the PS with a first light of a first wavelength; and
irradiating the tissue containing the PS with a second light of a second wavelength so as to treat the condition in the tissue,
wherein: (a) the PS absorbs light at the first wavelength and/or the second wavelength; and (b) the second light is more strongly absorbed by the tissue than the first light or the first light is more strongly absorbed by the tissue than the second light, so as to achieve a predetermined absorbed photon density gradient.

In certain embodiments, the condition is cancer and the tissue is mammalian.

In certain embodiments, the step of providing the PS comprises directly or indirectly administering to the tissue the PS or a precursor thereof.

In certain embodiments, the PS has a substantially constant absorption at the first wavelength and the second wavelength.

In certain embodiments, the PS is a Ru (II) or Os (II) or Rh (II) dyad.

In certain embodiments, the tissue is irradiated with at least one additional light not of the first or second wavelength, to further improve the absorbed photon density gradient.

In certain embodiments, the irradiating steps are conducted simultaneously or sequentially or with some overlap.

In certain embodiments, the first wavelength is within a hemoglobin absorption band, and the second wavelength is at a lowest effective attenuation coefficient of the tissue, or the second wavelength is within the hemoglobin absorption band, and the first wavelength is at the lowest effective attenuation coefficient of the tissue.

In certain embodiments, the first wavelength is in the visible range and the second wavelength is in the NIR range, or the second wavelength is in the visible range and the first wavelength is in the NIR range or the first wavelength is in the NIR range and the second wavelength is in the NIR range or the first wavelength is in the visible range and the second wavelength is in the visible range.

A second aspect of the invention comprises an apparatus adapted to conduct the method of the invention, wherein the apparatus comprises:

a first light source adapted to emit light at the first wavelength;
a second light source adapted to emit light at the second wavelength;
a power supply in electrical communication with the first and second light sources;
a focusing device adapted to focus the light from the first and second light sources on a common focal point; and
a controller adapted to adjust light emission from the first and second light sources such that the following equation is satisfied:

$$I(d)=I(\lambda_1 \text{ at } d=0)\times\exp(\mu_{\it{eff}}(\lambda_1)\times d)+I(\lambda_2 \text{ at } d=0)\times\exp(\mu_{\it{eff}}(\lambda_2)\times d),$$

where:
I is intensity;
$\lambda_1$ is the first wavelength;
$\lambda_2$ is the second wavelength;
d is a depth of the photosensitizer; and
$\mu_{\it{eff}}$ is population average tissue optical attenuation coefficient.

In certain embodiments of the apparatus, the first and second light sources comprise an Light Emitting Diode ("LED") array.

In certain embodiments of the apparatus, the first and second light sources are adapted to provide for spatial/temporal modulation of overlapping illumination spots using a spatial light modulator.

In certain embodiments of the apparatus, the first and second light sources comprise a volumetric emitting light source for interstitial or intracavity illumination by different wavelength for improved coupling into optical waveguides or optical fibers.

In certain embodiments of the apparatus, the first and second light sources are lasers.

In certain embodiments, the apparatus is adapted to enable a user to adjust a depth at which the PS is activated to match a depth of a target tumor.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference. The citation of any document is not to be construed as an admission that it is prior art with respect to the present invention.

DETAILED DESCRIPTION OF PREFERRED EMBODIMENTS OF THE INVENTION

Treatment Method

Within the concept of personalized medicine or personalized cancer medicine, it is expected that treatment methods will segment the target patient population increasingly depending on the up/down regulation of particular cell surface receptors, signaling pathways or other interfering biomolecules, in order to assess the most effective PS to deliver the cytotoxic dose.

While PDT equally has a cytotoxic dose given by the PS concentration and the photon density gradient inside the tissue, the indiscriminant damage to the tissue is mostly independent of the biochemical or molecular biological equilibrium in any given cell.

However, with the current prevailing attitude towards describing PDT delivery, a single excitation wavelength is utilized and hence the photon density gradient responsible for the cytotoxic dose gradient is fixed by the tissue's optical parameters, particularly its effective attenuation coefficient for ubiquitous available oxygen as is the case in infiltrating tumors. This limits the therapeutic efficacy of any given PS/excitation wavelength combination and an early (in situ) stage of the disease cannot be treated with the same combination as a more invasive manifestation of the same disease as the effective attenuation coefficient of the clinical target tissue determines the PDT dose gradient as well as the therapeutic selectivity of the disease.

However, if the PS can be excited across the wavelength spectrum to use simultaneous or sequential combinations of short strongly attenuated wavelength with longer weaker attenuated wavelength it is feasible to model the PDT dose effective gradient. For example, if one of the PS excitation wavelengths is at the edge of the hemoglobin absorption and one at the lowest attainable attenuation coefficient, theoretically any desired dose gradient can be achieved through the mixing of two exponential gradients.

The fraction of the two or more wavelengths to be used will be determined by the known distance to the base of the clinical target area from the light source. For this scheme to be successful, it is advantageous (albeit not necessary) that the PS absorption is flat across the intended wavelength range as given for the Ru, Os or Rh dyads; whereby, high q- and absorption as present in phthalocyanine and chlorophyll based PSs complicate the gradient calculations as the actual tissue concentrations of these PSs need to be known if they are comparable to the natural tissue chromophores.

Suitable PSs may, in certain embodiments, be prepared in accordance with the teachings of U.S. Patent Application Publication No. 20130331367.

Apparatus

The apparatus preferably includes a dosimetry feedback system to monitor the delivery of light in real time. The system can use the noninvasive subsurface monintoring and other elements of the apparatus disclosed in U.S. Pat. No. 6,413,267. The dosimetry feedback system may be used percutaneously, intravesically or intracorporeally depending on preferred application and monitors and adjusts, manually or automatically according to a predetermined or self adjusting algorithm, the source and hence distal peak or average power, time, frequency, pulse duration, wavelength or any combinations thereof in order to optimize the activation of the PSs. Preferred embodiments of the feedback system may utilize fiber optic fiber(s) or geometrical arrangements of these optical fibers to provide closed loop or open loop feedback to the dosimetry system.

Overall, this invention demonstrates that the number of thiophenes, the identity of the ancillary ligands, the scaffold employed (mononuclear versus dinuclear), and the nature of the metal can be used to fine-tune chemical, physical, and biological properties of the compounds to achieve photodynamic activity.

While the invention has been described in detail and with reference to specific examples thereof, it will be apparent to one skilled in the art that various changes and modifications can be made therein without departing from the spirit and scope thereof.

What is claimed is:

1. A method for treating a condition in a tissue, said method comprising the steps of:

providing a photosensitizer ("PS") within the tissue;

irradiating the tissue containing the PS with a first light of a first wavelength; and irradiating the tissue containing the PS with a second light of a second wavelength so as to treat the condition in the tissue, wherein:

(a) the PS absorbs light at the first wavelength and/or the second wavelength;

(b) the second light is more strongly absorbed by the tissue than the first light or the first light is more strongly absorbed by the tissue than the second light, so as to achieve a predetermined absorbed photon density gradient;

(c) detecting reflected light reflected from the tissue;

(d) adjusting emissions of the first light and the second light based on the reflected light detected and the following equation:

$$I(d) = I(\lambda_1 \text{ at } d=0) \times \exp(\mu_{\text{eff}}(\lambda_1) \times d) + I(\lambda_2 \text{ at } d=0) \times \exp(\mu_{\text{eff}}(\lambda_2) \times d),$$

where:

I is intensity;

$\lambda_1$ is the first wavelength;

$\lambda_2$ is the second wavelength;

d is a depth of the photosensitizer; and $\mu_{\text{eff}}$ is population average tissue optical attenuation coefficient;

(e) the first wavelength is within a hemoglobin absorption band, and the second wavelength is at a lowest effective attenuation coefficient of the tissue, or the second wavelength is within the hemoglobin absorption band, and the first wavelength is at the lowest effective attenuation coefficient of the tissue;

(f) the first light and the second light irradiate a common focal point simultaneously or with some overlap;

(g) spatial/temporal modulation of overlapping illumination spots is conducted; and (h) the PS is a Ru (II), Os (II) or Rh (I) dyad which is exogenous and is activated with the first light or the second light at a depth corresponding to a depth of a target tumor in the tissue so as to deliver a cytotoxically effective treatment to the target tumor in the tissue.

2. The method of claim 1, wherein the condition is cancer and the tissue is mammalian.

3. The method of claim 1, wherein the step of providing the PS comprises directly or indirectly administering to the tissue the PS or a precursor thereof.

4. The method of claim 1, wherein the PS has a substantially constant absorption at the first wavelength and the second wavelength.

5. The method of claim 1, wherein the tissue is irradiated with at least one additional light not of the first or second wavelength, to further improve the absorbed photon density gradient.

6. The method of claim 1, wherein the irradiating steps are conducted simultaneously.

7. The method of claim 1, wherein the first wavelength is within a hemoglobin absorption band, and the second wavelength is at a lowest effective attenuation coefficient of the tissue.

8. The method of claim 1, wherein the first wavelength is in the visible range and the second wavelength is in the near infrared range ("NIR"), or the second wavelength is in the visible range and the first wavelength is in the NIR range or the first wavelength is in the NIR range and the second wavelength is in the NIR range or the first wavelength is in the visible range and the second wavelength is in the visible range.

9. An apparatus for conducting the method of claim 1, said apparatus comprising:
a first light source configured to emit light at the first wavelength;
a second light source configured to emit light at the second wavelength;
a power supply in electrical communication with the first and second light sources;
a focusing device configured to focus the light from the first and second light sources on a common focal point;
detectors configured to detect the reflected light reflected from the tissue; and
a controller configured to adjust light emission from the first and second light sources,
wherein:
(a) the controller is configured to adjust light emission from the first and second light sources based on the reflected light detected by the detectors and the following equation:

$$I(d) = I(\lambda_1 \text{ at } d=0) \times \exp(\mu_{\mathit{eff}}(\lambda_1) \times d) + I(\lambda_2 \text{ at } d=0) \times \exp(\mu_{\mathit{eff}}(\lambda_2) \times d),$$

where:
I is intensity;
$\lambda_1$ is the first wavelength;
$\lambda_2$ is the second wavelength;
d is a depth of the photosensitizer; and
$\mu_{\mathit{eff}}$ is population average tissue optical attenuation coefficient (b) the first wavelength is within a hemoglobin absorption band, and the second wavelength is at a lowest effective attenuation coefficient of the tissue, or the second wavelength is within the hemoglobin absorption band, and the first wavelength is at the lowest effective attenuation coefficient of the tissue;

(c) the apparatus is configured to irradiate the common focal point with the light at the first wavelength and the light at the second wavelength simultaneously or with some overlap;

(d) the apparatus further comprises a spatial light modulator configured to provide for spatial/temporal modulation of overlapping illumination spots; and (e) the apparatus is configured to activate an exogenous photosensitizer (PS) with the light of the first wavelength or the light of the second wavelength at a depth corresponding to a depth of a target tumor in the tissue so as to deliver a cytotoxically effective treatment to the target tumor in the tissue, wherein the PS is a Ru (II), Os (II) or Rh (II) dyad.

10. The apparatus of claim 9, wherein the first and second light sources comprise a Light Emitting Diode ("LED") array.

11. The apparatus of claim 9, wherein the first and second light sources are configured to provide for the spatial/temporal modulation of the overlapping illumination spots using the spatial light modulator.

12. The apparatus of claim 9, wherein the first and second light sources comprise a volumetric emitting light source for interstitial or intracavity illumination by different wavelength for improved coupling into optical waveguides or optical fibers.

13. The apparatus of claim 9, wherein the first and second light sources are lasers.

14. The apparatus of claim 9, which is configured to enable a user to adjust a depth at which the PS is activated to match a depth of a target tumor.

* * * * *